United States Patent
Awarzamani et al.

[11] Patent Number: 5,821,401
[45] Date of Patent: Oct. 13, 1998

[54] GAS SENSOR

[75] Inventors: Assadollah Awarzamani, Markgroeningen, Germany; Peter Kolb, Farmington Hills, Mich.

[73] Assignee: Robert Bosch GmbH, Stuttgart-Feuerbach, Germany

[21] Appl. No.: 847,387

[22] Filed: Apr. 24, 1997

[30] Foreign Application Priority Data

Apr. 24, 1996 [DE] Germany .................. 196 16 341.2

[51] Int. Cl.[6] ............................................ G01N 7/00
[52] U.S. Cl. ............................................ 73/23.32; 338/34
[58] Field of Search .......................... 73/31.05, 23.32; 338/34; 204/425, 421, 424, 426

[56] References Cited

U.S. PATENT DOCUMENTS

| | | | |
|---|---|---|---|
| 4,450,428 | 5/1984 | Ohta | 338/34 |
| 4,591,423 | 5/1986 | Kato et al. | 338/34 |
| 5,329,806 | 7/1994 | McClanahan et al. | 73/31.05 |
| 5,467,636 | 11/1995 | Thompson | 73/23.31 |
| 5,602,325 | 2/1997 | McClanahan et al. | 73/23.31 |
| 5,616,825 | 4/1997 | Achey et al. | 73/31.05 |

FOREIGN PATENT DOCUMENTS 0 624 791  11/1994  European Pat. Off. .

Primary Examiner—George M. Dombroske
Assistant Examiner—Jewel Thompson
Attorney, Agent, or Firm—Spencer & Frank

[57] ABSTRACT

A gas sensor includes a one-piece housing sleeve having a length dimension; an exhaust gas-side end and an opposite, exhaust gas-remote end, an inner space, an external thread, a terminal length portion which includes the exhaust gas-side end and which is exposable to an exhaust gas and a shoulder extending along an entire inner circumference of the housing sleeve at the terminal length portion thereof. A protecting sleeve which is disposed in the terminal length portion has a sealing collar seated on the shoulder of the housing sleeve. A ceramic supporting member is disposed in the inner space and has a throughgoing aperture parallel to the length dimension of the housing sleeve. The ceramic supporting member separates the inner space into a reference gas chamber and an exhaust gas chamber. The exhaust gas chamber is surrounded by the terminal length portion of the housing sleeve. A sensor element passes through and is fixedly held in the throughgoing aperture of the ceramic supporting member.

15 Claims, 1 Drawing Sheet

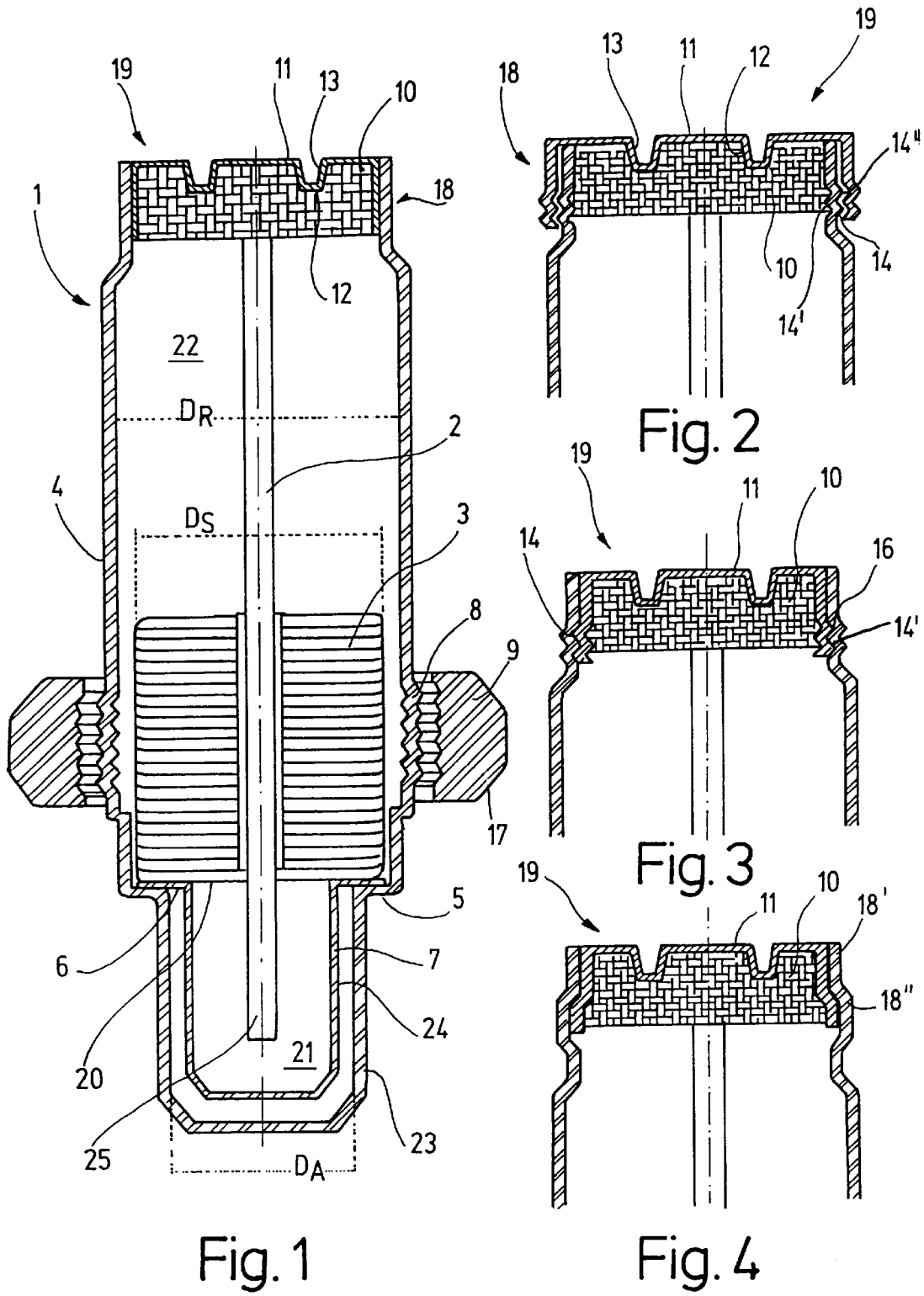

GAS SENSOR

CROSS REFERENCE TO RELATED APPLICATION

This application claims the priority of German Application No. 196 16 341.2 filed Apr. 24, 1996, which is incorporated herein by reference.

BACKGROUND OF THE INVENTION

This invention relates to a gas sensor, particularly for exhaust gases of internal-combustion engines. The gas sensor has a planar sensor element which is disposed in a tubular housing and which is held in a longitudinal bore of a ceramic supporting member separating a reference gas chamber from an exhaust gas chamber.

Gas sensors of the above-outlined type are known. For example, published European Patent Application 0 624 791 describes a gas sensor in which a planar sensor element is disposed in a housing of complex structure. The housing is tubular and has a lip extending circumferentially at the outside of the housing for receiving and immobilizing a nut which, in turn, is so structured that the sensor may be mounted in an exhaust gas system of, for example, an automotive vehicle. The known housings for planar sensor elements thus have the disadvantage that they are of complex construction and therefore their manufacture as well as assembly involves substantial expense.

SUMMARY OF THE INVENTION

It is an object of the invention to provide an improved gas sensor of the above-outlined type from which the discussed disadvantages are eliminated.

This object and others to become apparent as the specification progresses, are accomplished by the invention, according to which, briefly stated, the gas sensor includes a one-piece housing sleeve having a length dimension, an exhaust gas-side end and an opposite, exhaust gas-remote end, an inner space, an external thread, a terminal length portion which includes the exhaust gas-side end and which is exposable to an exhaust gas and an inwardly projecting shoulder extending along an entire inner circumference of the housing sleeve at the terminal length portion thereof. A protecting sleeve which is disposed in the terminal length portion has a sealing collar seated on the shoulder of the housing sleeve. A ceramic supporting member is disposed in the inner space and has a throughgoing aperture parallel to the length dimension of the housing sleeve. The ceramic supporting member separates the inner space into a reference gas chamber and an exhaust gas chamber. The exhaust gas chamber is surrounded by the terminal length portion of the housing sleeve. A sensor element passes through and is fixedly held in the throughgoing aperture of the ceramic supporting member.

Thus, the gas sensor according to the invention as outlined above has the advantage that the housing containing the sensor element has been significantly simplified because the housing is a one-piece component shaped as a sleeve which is closed at the exhaust gas side and which may be threaded easily into the exhaust gas system. No welding or other connecting operations have to be performed in the manufacture of the gas sensor. The making of the gas sensor is simplified because the required individual components are reduced in number, and the assembly is less complex. Since the housing sleeve of the gas sensor according to the invention needs no welds, no stress-caused deformation of material will occur. The housing sleeve according to the invention is advantageously made only of a single material, preferably a metal so that an improved, more homogenous thermal behavior is obtained.

The invention also relates to a sleeve-sealing assembly which is situated at the exhaust gas-remote end of the gas sensor. The sleeve-sealing assembly is particularly adapted for use in a gas sensor of the above-outlined type and serves for improving the high-temperature resistance and seal of the exhaust gas-remote end of the gas sensor (cable pass-through region) against external effects such as water. The sleeve-sealing assembly is formed of a plug composed of a preferably high-temperature resistant elastomer and a preferably metal closure cap. By virtue of the special shape of the closure cap and the elastomer, particularly their conical interengaging relationship, a particularly satisfactory sealing effect is achieved upon heating and simultaneous expansion of the elastomer and determined zones of the closure cap.

BRIEF DESCRIPTION OF THE DRAWING

FIG. 1 is a schematic longitudinal sectional view of a gas sensor according to a preferred embodiment of the invention.

FIG. 2 is a fragmentary longitudinal sectional view of a gas sensor, showing a preferred embodiment of a sensor sealing assembly.

FIG. 3 is a fragmentary longitudinal sectional view of a gas sensor, showing another preferred embodiment of a sensor sealing assembly.

FIG. 4 is a fragmentary longitudinal sectional view of a gas sensor, showing a further preferred embodiment of a sensor sealing assembly.

DESCRIPTION OF THE PREFERRED EMBODIMENTS

FIG. 1 shows a gas sensor generally designated at 1, having a one-piece metal housing sleeve 4 which, with an end portion, projects into a non-illustrated exhaust gas system to be exposed to the exhaust gas contained therein. A planar sensor element 2 is accommodated in the sleeve 4 and is, in its mid region, coaxially and in a gastight manner surrounded by a cross-sectionally circular ceramic supporting member 3 having a diameter $D_s$. The ceramic member 3 separates a reference gas chamber 22 from an exhaust gas chamber 21 situated in the sleeve 4. The exhaust gas chamber 21 is situated in the exhaust gas system-side (hereafter "exhaust gas-side") of the gas sensor 1, whereas the reference gas chamber 22 is located remote from the exhaust gas system (hereafter "exhaust gas-remote"). Accordingly, the sleeve 4 has opposite, exhaust gas-side and exhaust gas-remote ends. The sleeve 4 is closed at its exhaust gas-side end at the system, except for apertures to allow passage of the exhaust gas into the interior of the sleeve 4. The metal sleeve 4 has a radially inwardly extending shoulder 5 about its entire circumference and has, in the reference gas chamber 22, an inner diameter $D_R$ which is greater than the inner diameter $D_A$ of the exhaust gas chamber 21. A sealing collar 6 is supported on the inner face of the shoulder 5 inside the sleeve 4. The sealing collar 6 is part of an inner protecting sleeve 7 which surrounds the exhaust gas-side region 25 of the sensor element 2. The ceramic supporting component 3 whose diameter $D_S$ is greater than the diameter $D_A$ of the exhaust gas chamber 21 lies with its exhaust gas-remote face 20 on the sealing collar 6 of the inner protecting sleeve 7 and presses the sealing collar 6 against the shoulder 5 to thus seal the region between the sealing collar 6, the ceramic member 3 and the sleeve 4. The exhaust gas-side zone 24 of the inner protecting sleeve 7 is, similarly to the part 23 of the sleeve 4, provided apertures (such as holes and/or slots) to ensure access of the exhaust gas to the exhaust gas chamber 21. The inner protecting sleeve 7 may be made of stainless steel or a chromium-nickel alloy.

The sleeve 4 has, in its region spaced from the shoulder 5 in a direction away from the exhaust gas side, an external thread 8 which is threadedly engaged by a threaded component 9. The latter preferably has a standardized outer thread for installing the sensor, for example, in a muffler of an exhaust gas system. An arbitrary, excessive turning (tightening) of the threaded part 9 on the sleeve 4 is prevented by a defined number of turns in the thread, by the shape and location of the thread as well as a conical terminal portion of the sleeve 4 in the zone 23 of the sleeve 4.

It is particularly advantageous to make the sleeve 4 from a single piece of sheet metal by stamping a rectangular blank, and then rolling and closing the same by a longitudinal seam, for example, by welding or soldering. The sleeve according to the invention is thus made from few individual components in a simple assembling operation.

The exhaust gas-remote cable exit (pass-through) region 18 of the gas sensor 1 (that is, its exhaust gas-remote end) is closed in a gas and liquid-tight manner by a plug 19 composed of a high-temperature resistant elastomer 10 and a metal closure cap 11. The closure cap 11 has conical beads 13 projecting inwardly to ensure a form-fitting interengagement with complemental, conical depressions 12 of the elastomer 10 which is preferably a component cast into the closure cap 11. By means of such a special shape of the closure cap 11 and the elastomer 10, the latter, when exposed to high temperatures and a resulting tendency to expand, may not escape and thus seals the inside of the metal sleeve 4 against the external environment. Likewise, by virtue of the expansion of the closure cap 11 and the beads 13 as a result of high temperatures, a pressure on the elastomer 10 is generated which contributes to improved sealing properties at high temperatures. In the described embodiment according to FIG. 1, the plug 19 is inserted in the cable outlet region 18 of the gas sensor 1 and seals the outgoing, non-illustrated Teflon cables; that is, the plug 19 has non-illustrated apertures for the passage of the cables. The seal of the gas sensor 1 in the cable outlet region 18 increases the high-temperature resistance and sealing properties of the cable outlet of the gas sensor 1 against external effects such as water.

FIG. 2 illustrates a further embodiment of a sealing assembly for closing the exhaust gas-remote end of the gas sensor 1. According to this embodiment, the cable outlet region 18 of the sleeve 4 has a rolled-on thread 14 such that the sleeve wall in its entire thickness is deformed, whereby an inner and an outer thread 14', 14" is obtained. The outer thread 14" threadedly receives the closure cap 11 which is provided with beads 13 as well as the elastomer 10 so that the thus-formed plug 19 protects the inside of the sleeve 4 and the cable passages against external effects.

FIG. 3 illustrates a further embodiment of a sealing plug 19 for the exhaust gas-remote end (that is, the cable outlet region 18) of the gas sensor 1. According to this embodiment, the elastomer 10 is introduced into the closure cap 11 which, by its outer thread 16, is screwed on an inner thread 14' of the sleeve 4.

FIG. 4 shows a further embodiment of an exhaust gas-remote sealing assembly for the gas sensor 1. According to this embodiment, the inner diameter of the cable outlet region 18 of the sleeve 4 is not uniform; in the terminal region 18' the diameter is less than that of a region 18" which is situated immediately ahead of the terminal region 18'. Conversely, the plug 19 composed of the elastomer 10 and the closure cap 11 has in its region oriented towards the exhaust gas side, an outer diameter which is greater than that of the region oriented away from the exhaust gas side. Such a sealing assembly may be made, for example, by embossing or pressing.

It is to be understood that other combinations and arrangements of the elastomer, the closure cap and the configuration of the cable outlet region 18 of the sleeve 4 are feasible as long as the high-temperature resistant elastomer and the closure cap cooperate with one another in such a manner that particularly in case of temperature increase a very pronounced sealing effect against external effects is obtained.

The described plug 19 made of an elastomer 10 and a closure cap 11 is not limited to a use in gas sensors containing planar sensor elements according to the invention but may find application with any type of sensor element.

It will be understood that the above description of the present invention is susceptible to various modifications, changes and adaptations, and the same are intended to be comprehended within the meaning and range of equivalents of the appended claims.

What is claimed is:

1. A gas sensor comprising
   (a) a one-piece housing sleeve having
      (1) a length dimension;
      (2) an exhaust gas-side end and an opposite, exhaust gas-remote end;
      (2) an inner space;
      (3) an external thread;
      (4) a terminal length portion including said exhaust gas-side end; said terminal length portion being exposable to an exhaust gas; and
      (5) a shoulder extending along an entire inner circumference of said housing sleeve at said terminal length portion;
   (b) a protecting sleeve disposed in said terminal length portion and having a sealing collar seated on said shoulder;
   (c) a ceramic supporting member disposed in said inner space; said ceramic supporting member having a throughgoing aperture parallel to said length dimension; said ceramic supporting member separating said inner space into a reference gas chamber and an exhaust gas chamber; said exhaust gas chamber being surrounded by said terminal length portion; and
   (d) a sensor element passing through and fixedly held in said throughgoing aperture of said ceramic supporting member.

2. The gas sensor as defined in claim 1, wherein said ceramic supporting member has an end face oriented towards said exhaust gas-side end; said end face being seated on said sealing collar for providing a gas tight seal between said shoulder and said ceramic supporting member.

3. The gas sensor as defined in claim 1, wherein said exhaust gas chamber has an inner diameter smaller than an inner diameter of said reference gas chamber.

4. The gas sensor as defined in claim 1, wherein said ceramic supporting member has a diameter greater than an inner diameter of said exhaust gas chamber.

5. The gas sensor as defined in claim 1, wherein regions of said housing sleeve and said protecting sleeve adjoining said exhaust gas-side end are provided with apertures.

6. The gas sensor as defined in claim 1, further comprising an internally threaded component screwed on said outer thread of said housing sleeve.

7. The gas sensor as defined in claim 1, further comprising a plug closing said exhaust gas-remote end of said housing sleeve; said plug being composed of an elastomer and a closure cap containing said elastomer.

8. The gas sensor as defined in claim 7, wherein said closure cap is a metal.

9. The gas sensor as defined in claim 7, wherein said plug is inserted into said exhaust gas-remote end of said housing sleeve.

10. The gas sensor as defined in claim 7, wherein said plug is screwed into said exhaust gas-remote end of said housing sleeve.

11. The gas sensor as defined in claim 10, wherein said plug is screwed into an additional external thread at said gas-remote end of said housing sleeve.

12. The gas sensor as defined in claim 7, wherein said plug is pressed into said gas-remote end of said housing sleeve.

13. The gas sensor as defined in claim 7, wherein said elastomer is high-temperature resistant.

14. The gas sensor as defined in claim 7, wherein said closure cap has a first configuration and said elastomer has a second configuration; said first and second configurations are in an interleaving relationship with one another.

15. The gas sensor as defined in claim 14, wherein said first configuration comprises conical protrusions and said second configuration comprises conical depressions; said conical protrusions complementally fitting into said conical depressions.

* * * * *